(12) United States Patent
Siegel et al.

(10) Patent No.: US 6,411,085 B1
(45) Date of Patent: Jun. 25, 2002

(54) METHOD FOR DETECTING DEFECTS IN WORK PIECES AND FACILITY AND MAGNETIC FIELD MEASURING APPARATUS FOR IMPLEMENTING SAID METHOD

(75) Inventors: Michael Siegel, Düren; Yuri Tavrin, Salzdetfurth; Karl Schreiber, Mellensee; Armin Plath, Birmingham, all of (DE)

(73) Assignees: Forschungszentrum Julich GmbH, Julich; Rolls-Royce Deutschland LTD & CO KG, Dahlewitz, both of (DE)

( * ) Notice: Subject to any disclaimer, the term of this patent is extended or adjusted under 35 U.S.C. 154(b) by 0 days.

(21) Appl. No.: 09/529,741
(22) PCT Filed: Oct. 19, 1998
(86) PCT No.: PCT/EP98/06600
§ 371 (c)(1),
(2), (4) Date: Apr. 18, 2000
(87) PCT Pub. No.: WO99/21000
PCT Pub. Date: Apr. 29, 1999

(30) Foreign Application Priority Data

Oct. 20, 1997 (DE) ........................... 197 46 000

(51) Int. Cl.[7] ............... G01R 33/12; G01N 27/72; G01N 27/82
(52) U.S. Cl. ................ 324/240; 324/260
(58) Field of Search ................ 324/235, 239, 324/240, 241, 242, 243, 260

(56) References Cited

U.S. PATENT DOCUMENTS

| 4,864,233 A | 9/1989 | Harrison |
| 5,006,800 A | 4/1991 | Hedengren et al. |
| 6,157,190 A | * 12/2000 | Nagaishi et al. ............ 324/235 |

FOREIGN PATENT DOCUMENTS

| DE | 39 23 377 C1 | 6/1990 |
| DE | 41 26 810 A1 | 4/1993 |
| DE | 42 15 358 A1 | 11/1993 |
| DE | 43 42 100 A1 | 7/1995 |
| EP | 0 308 888 A2 | 3/1989 |

OTHER PUBLICATIONS

"SQUIDS for nondestructive evaluation" By Jenks et al., J.Phys. D:Appl. Phys. 30 (1997) pp 293–323.
"A second–order SQUID gradiometer operating at 77 K" by Tavrin et al., Supercond. Sci. Technol. 7 (1994) pp 265–268.

* cited by examiner

Primary Examiner—Walter E. Snow
(74) Attorney, Agent, or Firm—Herbert Dubno

(57) ABSTRACT

A depth and other characteristics of a ferromagnetic impurity in a workpiece of nonmagnetic material can be determined after demagnetizing of the workpiece by magnetizing the workpiece in a uniform field, preferably to saturation, and thereafter taking measurements of the field strength from the impurity at two different distances, forming a quotient or ratio of the measured values and determining the depth from a curve in which the signal ratio or quotient is plotted against the depth.

10 Claims, 5 Drawing Sheets

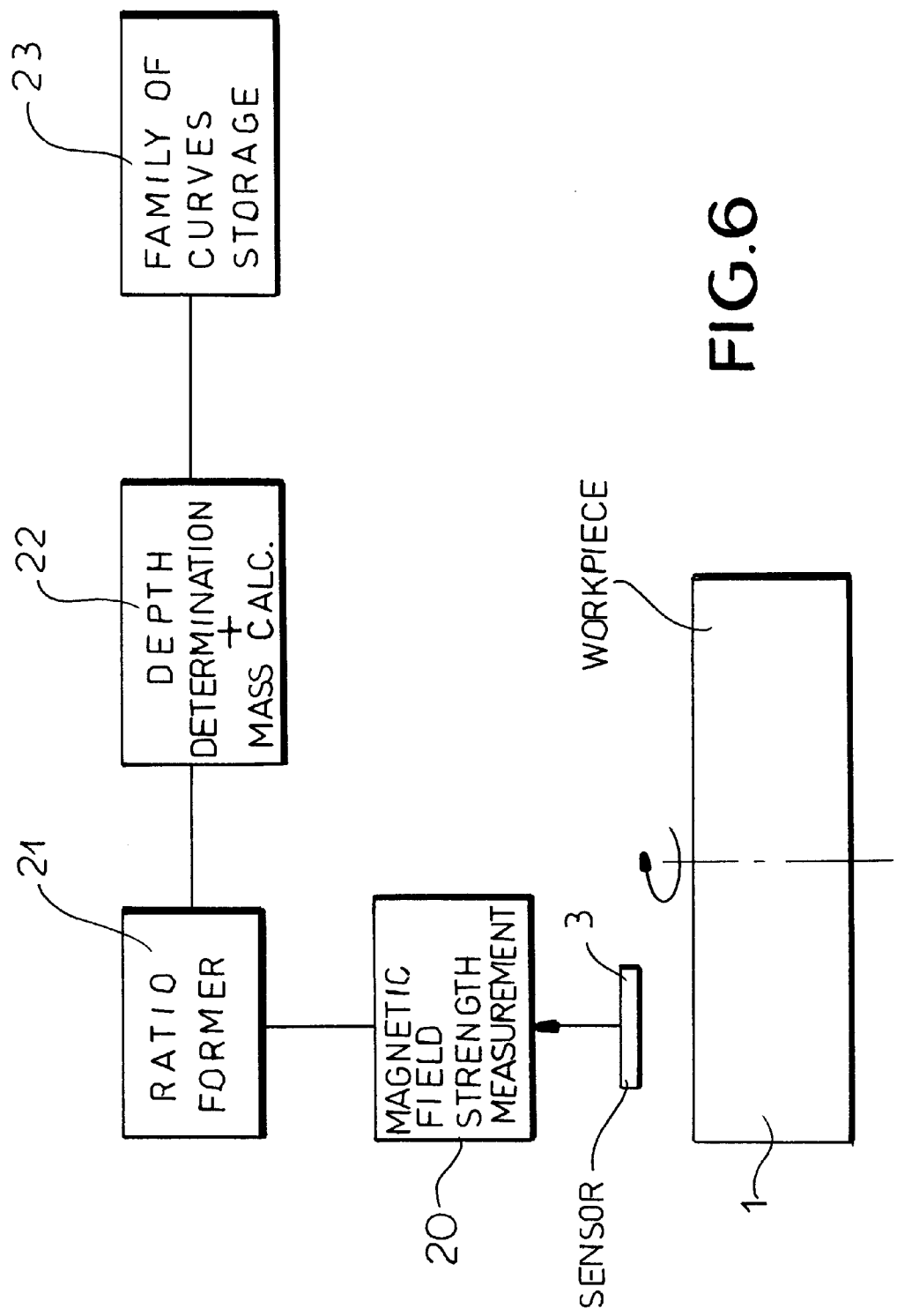

Figure 1:
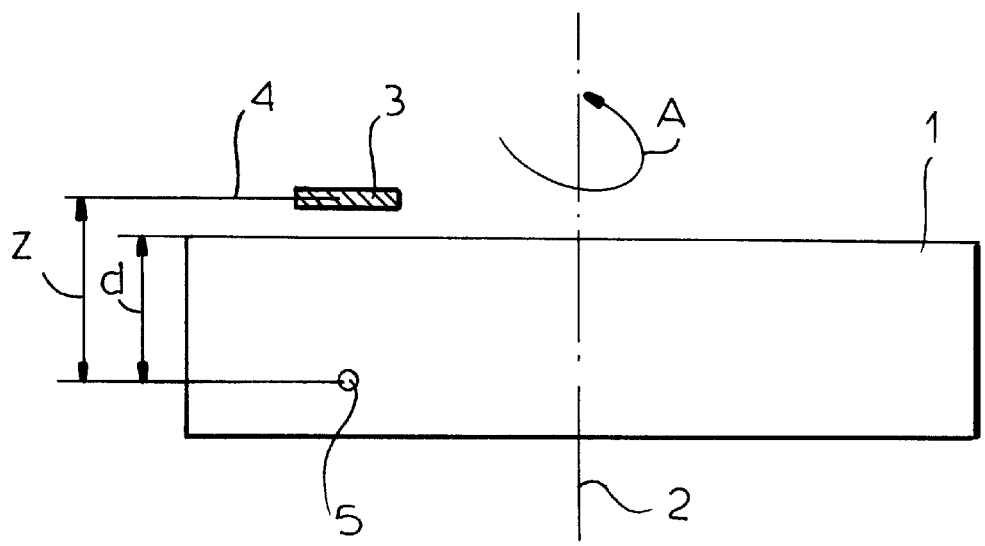

METHOD FOR DETECTING DEFECTS IN WORK PIECES AND FACILITY AND MAGNETIC FIELD MEASURING APPARATUS FOR IMPLEMENTING SAID METHOD

The invention relates to a process for determining ferromagnetic impurities in workpieces in nonmagnetic material, especially in wheel disks or shafts of gas turbines for aircraft or the like. It relates further to an apparatus for carrying out the process and a magnetic-field measuring device, especially as a part of this apparatus.

In machine construction practice, increasingly workpieces of components under this designation of nonmagnetic materials, especially nickel-based materials or titanium materials are made so that the workpieces will have high mechanical and/or thermal loading resistances. This applies above all for components of aircraft gas turbines since materials used for them have the smallest possible specific gravity.

This applies especially to nickel-based alloys and titanium-based alloys. In the course of metallurgical fabrication processes, iron-containing impurities enter these alloys. These impurities give rise to defects in the microstructure of the material and affect thereby the mechanism loadability of the workpiece. They are referred to as defects and because of their iron content, as ferromagnetic defects. Depending upon the size and number of the impurities and their spatial locations in the workpiece, the workpiece can be damaged by certain mechanical loads, leading to the destruction of the workpiece. Since ferromagnetic impurities can always be contained in a nickel-based alloy or a titanium-based alloy, for every concrete use and loading associated therewith there is a certain permissible mass, i.e. size of the impurities and their spatial positions in a workpiece which can be established. This maximum permissible mass of impurities is designated as the critical mass.

Especially critical with respect to the aforementioned impurities, are components or workpieces for aircraft gas turbines since, in these cases, the durability requirements are especially high. This applies even for the production of the respective workpieces, especially the wheel disks carrying the rotor blades or also the shafts of an aircraft turbine in which the mass of the ferromagnetic impurities in the workpieces or a blank thereof should be detected before this workpiece is further processed and especially built into the aircraft turbine. The latter should take place only when the determined mass of the possibly-present impurities is less than the above-mentioned critical mass for such impurities.

Basically three processes for the detection of ferromagnetic impurities are useable, namely, X-ray tomography, ultrasonic measurements and magnetoscope measurements.

By means of X-ray tomography, impurities can be detected based upon their different compositions and the X-ray contrasts associated therewith. X-ray tomography is, however, extremely time-consuming, very expensive and outside routine processes in a production sequence. The method is in any case used for comparative measurements and for calibrating of the processes.

An ultrasonic measurement detects impurities based upon their different densities. By the scattering of the ultrasound crystallites of the basic alloy, the contrast is significantly reduced. The method is therefore suitable only for larger impurities in workpieces which are not very thick.

The magnetoscope measuring process utilizes the fact that the aforedescribed impurities are ferromagnetic. In the process, a magnetic-field measuring device with a magnetic-field sensor is used which contains a magnet by means of which the impurities are magnetized. Simultaneously the measurement of the magnetic signals of the magnetized impurities is carried out.

The magnetoscope process has, however, in its known form, a series of drawbacks. Since the magnetization occurs only in the measurement region, impurities are differently magnetized depending upon their depths within the workpiece. Since the magnetic induction of the magnetizing device decreases with the third power of the distance, the impurities at the greatest distance from the magnetic-field sensor are only extremely weakly magnetized and are thus not detected by it. Furthermore, the magnetic field as a consequence of its point-like effect is inhomogeneous which has, as a consequence, that the magnetic signals of the impurities differ depending upon their [the impurities] orientation with respect to the magnetizing device. Because of the under-defined magnetizing state, conclusions cannot be made as to the mass of the impurities and their depths in the workpiece.

It is the object of the invention to provide a process suitable for serial production which can enable detection of ferromagnetic impurities in nonmagnetic workpieces precisely, reliably and in a simple manner.

A further object is to conceive an apparatus for carrying out this process and a magnetic-field measuring device associated therewith.

As far as the process goes, the objects are achieved according to the invention in that the workpiece is subjected to a magnetic field, the impurities at least in sections of the workpiece are uniformly magnetized and the workpiece is thereafter fed to a magnetic-field measuring device and there the magnetic signals of the respective impurity is measured.

The basic thought of the invention is that the workpiece or the impurities, prior to the specific measurement by means of a magnetization process is brought into a magnetically-ordered and thus defined state and only thereafter is a respective magnetic signal of an impurity detected with the aid of the magnetic-field measuring device, for example, by a suitable scanning, i.e. relative movement between the magnetic-field sensor and workpiece. Thus the requirement is satisfied that a particular impurity is not detected exclusively with respect to its position but also with respect to its mass in a relatively precise manner.

It is worth carrying out the process with a through-magnetization so that the impurities are magnetized to saturation. In most applications, however, a magnetization is sufficient which does not reach the saturation limits for generating magnetic signals from the impurities.

In any case it is advantageous for the workpiece to be subjected to a substantially homogeneous magnetic field. To the extent that the workpiece is subjected at an earlier point in time to a stronger magnetic field than the magnetization field strength applied, before the magnetization [from which the signal is to be obtained], a demagnetization should be effected.

In a further embodiment of the invention it is provided that the workpiece is scanned in a scanning plane with the magnetic measuring device and the position of the impurities determined with reference to this plane in this manner. For detecting the depth of the respective impurity in the workpiece, it is possible basically to scan the workpiece in a further scanning plane, preferably lying transversely to the first.

According to the invention however, the following features are proposed for determining the depths of the respective impurities in the workpiece:

(a) Detection of the signal of the impurity at a first distance between the magnetic-field sensor and the surface of the workpiece;

(b) Detection of the signal from the impurity at a second distance between the magnetic-field sensor and the surface of the workpiece;

(c) Forming a signal ratio as a quotient of the measurement signal from the two detected signals from the impurity;

(d) Determining the depth based upon a curve which portrays the dependency between the signal ratio and the depth.

Thus the depth measurement is effected starting from the first scanning plane by two measuring steps at different distances from the surface of the workpiece to form a signal ratio and by subsequent marking off from a curve portraying the dependency between the single ratio and depth. The term "curve" is here understood in its most general form. It can be in a graphic form or in the form of a matrix or function. It will be understood that it is established initially by corresponding calibration and then firmed up. It has been found that with this method in a simple way and without large expenditure for apparatus, a relatively exact indication as to the depth arrangement of respective impurities of concern can be obtained.

Once the depth of the impurities is determined, mass of the impurities can also be established. For this purpose, the invention makes use of the following alternative proposals.

With one proposal, a curve is selected from a family of curves which display the relationship between mass and measurement signals at various depths and the mass is then established. By selection of the curve, the mass can be marked off directly based upon the measurement signal.

Alternatively, the mass of the impurity can also be established by development of a family of curves which display the relationship between the depth of the impurities and their measurement signals for different masses. Based upon the measurement signal and the determined depth, a curve can be selected which represents the respective mass of the impurity.

The second part of the object of the invention is achieved, in accordance with the invention with an apparatus for carrying out the aforedescribed process and which is characterized by the following features:

(a) A magnetization device for substantially uniformly through-magnetizing a workpiece by generating a substantially homogenous magnetic field whether in sections or over the whole [of the workpiece]—and (b) A magnetic-field measuring device for detecting magnetic signals of an impurity.

It will be self-understood that this apparatus can be comprised on the one hand from two separate units or on the other hand by a combination device. Thus it is advantageous on the grounds indicated earlier to enable the magnetization device to be capable of through-magnetizing of impurities up to saturation. For the case in which the workpiece is already premagnetized, it is advantageous that the apparatus also include a demagnetization unit so that the magnetization of the workpiece depends upon the effect of the magnetizing device and on the premagnetization.

The magnetic-field measuring unit itself, whether as part of the aforedescribed apparatus or independently thereof, is characterized by the following features according to the invention:

(a) the magnetic-field sensor is movable in a scanning plane;

(b) the magnetic-field sensor in movable perpendicular to the scanning plane between two measurement positions;

(c) the magnetic-field measuring device has a device for calculating the signal ratio of the measured signals at the two measuring points;

(d) in the magnetic-field measuring device a curve is stored which represents the dependency between the signal ratio and the depth of the impurity in the workpiece;

(e) the magnetic-field measuring device has a device for calculating the depth of an impurity based upon the determined signal ratio and the curve.

With such a magnetic-field measuring device, a particular impurity can be relatively exactly localized and, in particular, by scanning in the scanning plane on the one hand and on the other by detection of the magnetic signals at two different distances to the scanning plane, whereby the scanning plane advantageously lies parallel to one of the surfaces of the workpiece.

As already indicated above, the storage of the curve in the magnetic-field measuring device can be effected in various ways. Important only is that it can be incorporated in the calculating process at the end of which a signal corresponding to the depth of the impurity is obtained which can then preferably be digitally displayed.

For the additional determination of the mass of a certain impurity, according to the invention, two possible embodiments can be used. One of them is characterized by the following features:

(a) in the magnetic-field measuring device, a family of curves for different depths is stored which relate the dependency between mass and measurement signal at different depths.

(b) the magnetic-field measuring device has a device for calculating mass of the impurity from the family of curves by selection of the curve corresponding to the determined depth and from the measurement signal.

Alternatively thereto, the following embodiment is provided:

(a) a family of curves for different mass is stored in the magnetic-field measuring device and relates the dependency between depth and measurement signals for different masses;

(b) the magnetic-field measuring device has a device for calculating the mass of the impurity from the measurement signal and the determined depth.

As the magnetic-field measuring device, basically all known devices for determining the magnetic fields can be considered. An especially good resolution can be obtained with the aid of a second-order gradiometer with a superconductive quantum interferometer (SQUID) on the basis of a high-temperature superconductor. Such magnetic-field measuring devices are known per se as state of the art (Tavrin, Chang, Wolf and Braginski, A second-order SQUID-gradiometer operating at 77K, Supercond. Sci. Technol. 7 (1994), P. 265 to 268; Jenks, Sadeghi and Wikswo, SQUIDS for non-destructive evaluation, Appl. Phys. 30 (1997) S. 293 to 323. They can also detect impurities at depths of 50 mm depending upon their orientation and mass with precision and are suitable also for routine processes in the production of such workpieces.

Figure 2:
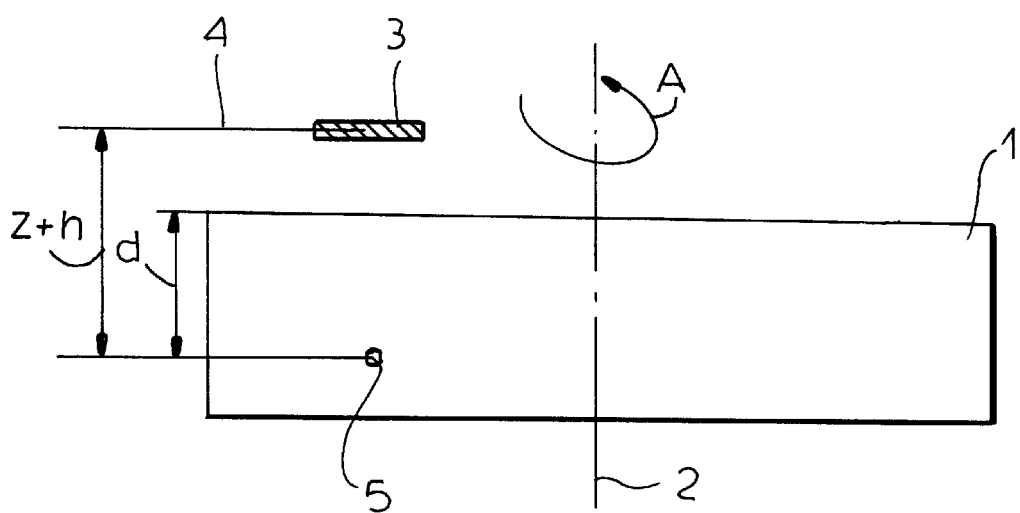
Figure 3:
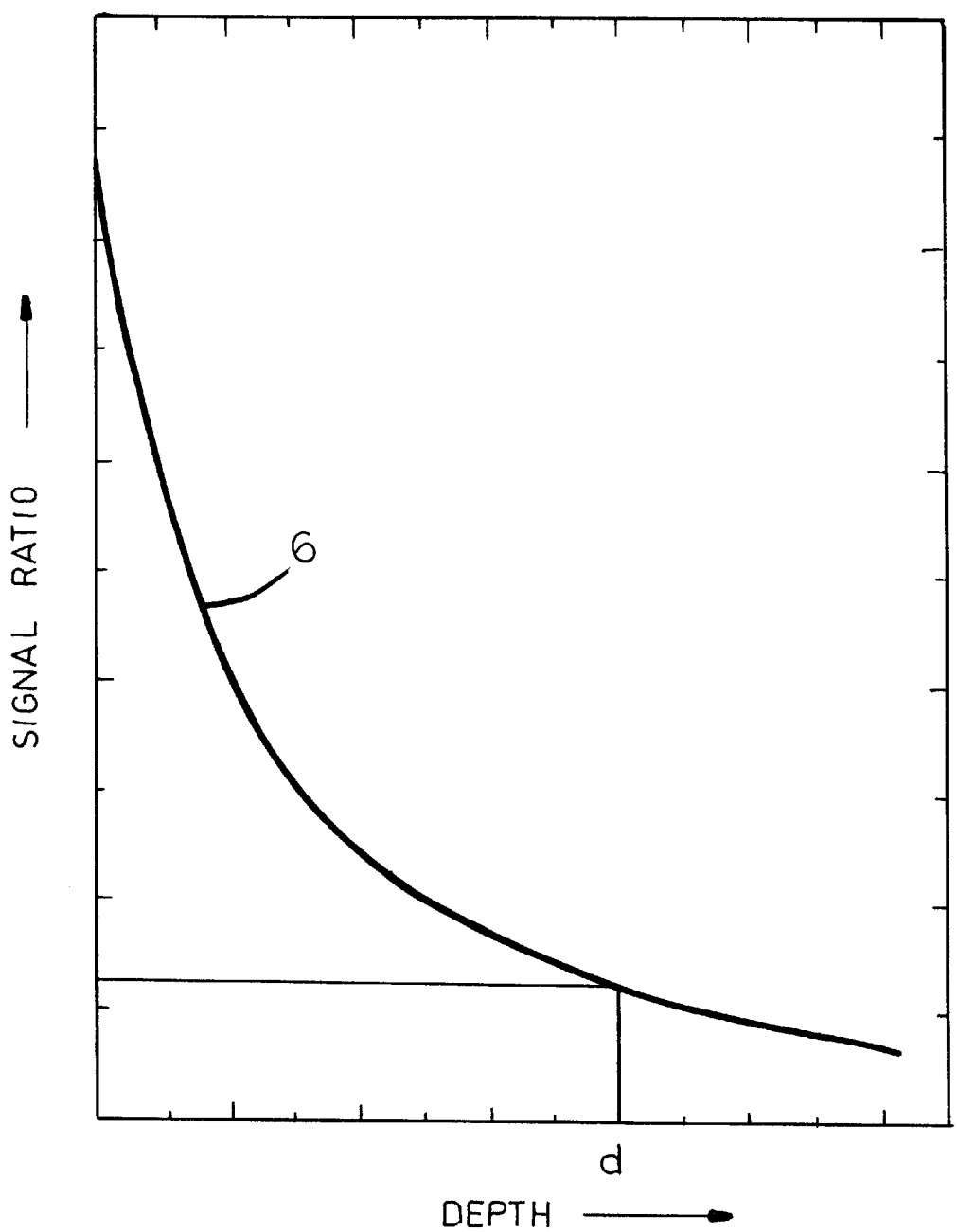
Figure 4:
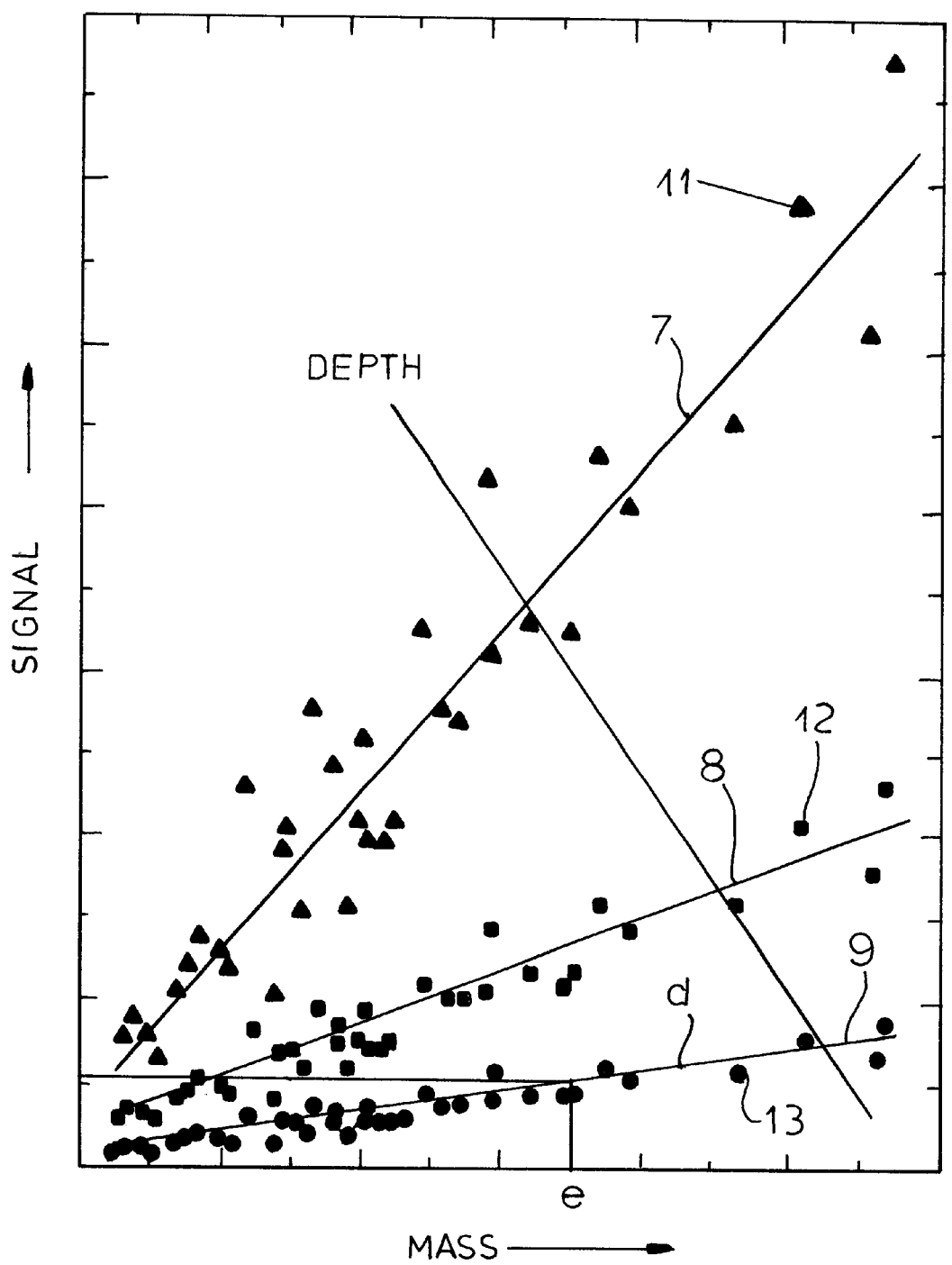
Figure 5:
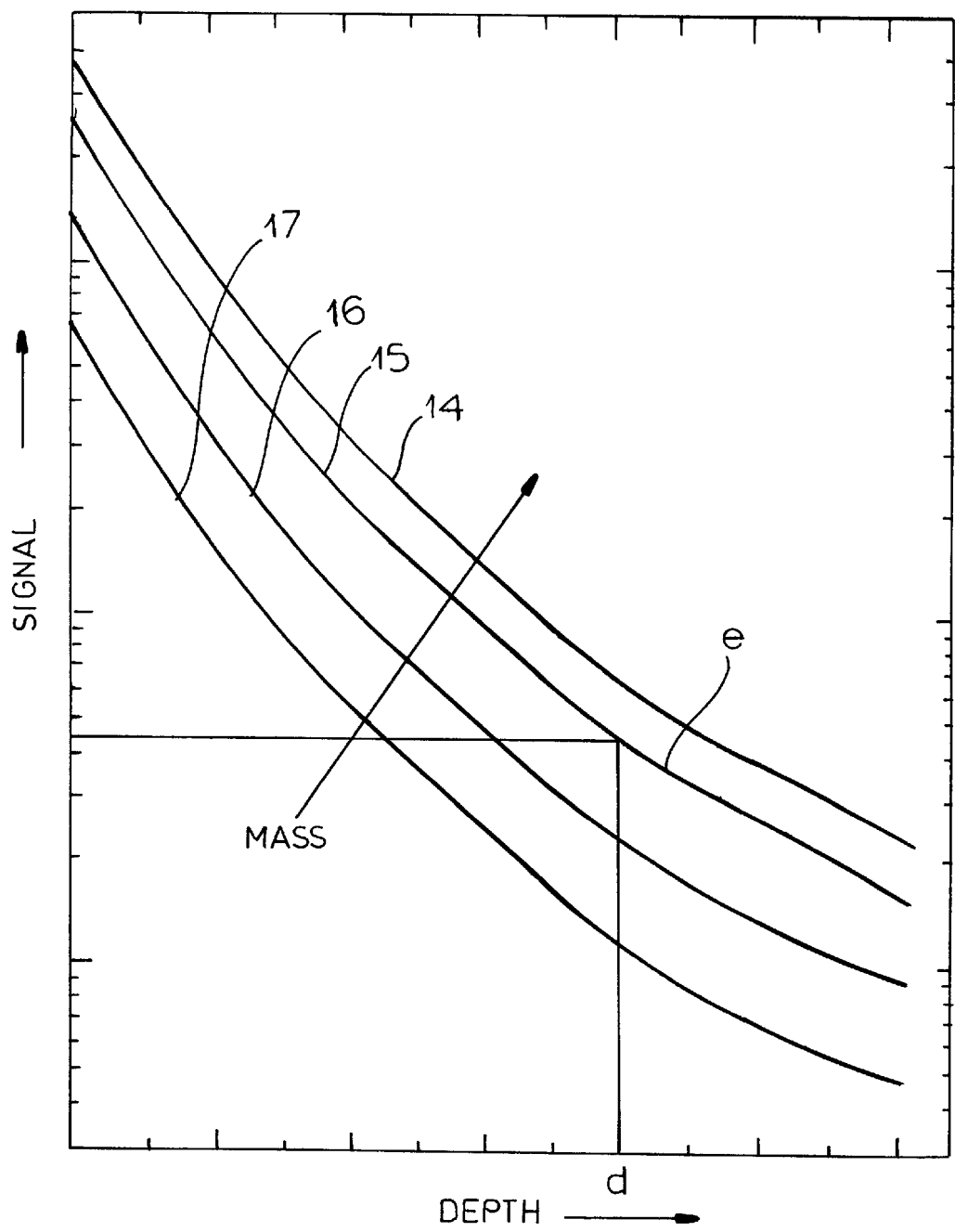

The invention is described in greater detail with reference to an embodiment shown in the drawing. It shows:

FIG. 1 the side elevation of a disk-shaped workpiece with a magnetic-field sensor in a first measurement position;

FIG. 2 the illustration of FIG. 1 with a magnetic-field sensor in a second measurement position;

FIG. 3 a graph illustrating the relationship between the signal ratio of the measurement signal from the two measurement positions and the depth of an impurity in the workpiece;

FIG. 4 a graph showing the relationship between a measurement signal and the mass of an impurity in a workpiece at different depths;

FIG. 5 a graph showing the relationship between a measurement signal and the depth of an impurity in a workpiece for different masses; and FIG. 6 is a block diagram.

SPECIFIC DESCRIPTION

FIGS. 1 and 2 show in a simplified illustration, a disk-shaped rotationally symmetrical workpiece 1, which is rotatably journaled in a workpiece holder not shown here in greater detail so as to be rotatable about the axis 2. The rotation direction is indicted by the arrow A.

Above the workpiece a magnetic-field sensor 3 can be seen. It is part of a magnetic-field measuring device not shown here in greater detail, in the form of a second-order gradiometer with a superconductive quantum interferometer (SQUID) on the basis of a high-temperature superconductor. The magnetic-field sensor 3 is separate from or part of the magnetic-field measuring device and is movable in a horizontal scanning plane 4 whereby it allows scanning of the entire surface of the workpiece 1 taking into consideration the rotational symmetry of the workpiece 1 and its rotational mounting when it is horizontally-displaceable in the radial direction, i.e. in the plane of the drawing. The apparatus elements required for this purpose have been partly omitted for clarity.

In the workpiece 1, overdimensionally-enlarged, there is a ferromagnetic impurity 5 located at a vertical distance z from the scanning plane 4 and thus from the magnetic-field sensor 3. The latter is held directly above the impurity 5 at scanning, this position in the horizontal plane being detected by the above-described scanning and, indeed being established from the maximum of the magnetic signal obtained. Initially the workpiece 1 was, in a separate magnetizing device not here shown, subjected over its entire volume to a homogeneous magnetic field so that the ferromagnetic impurities in it reach a defined uniform magnetization state.

After positioning the workpiece 1, a magnetic-field sensor 3 in the illustrated first measurement position, a first measurement process is commenced. Based upon the magnetic signal from the impurity 5, a first measurement signal is detected. Thereafter, the magnetic-field sensor 3 is moved by a magnitude h perpendicular to the surface of the workpiece 1 upwardly into a second measurement position as is visible from the two. The magnetic-field sensor 3 now is at a distance z+h from the impurity 5. By a new measurement process, a second measurement signal is obtained that, because of its greater distance form the impurity 5, is weaker than the first. It will be self-understood that in the measurements applied to other impurities, the difference h between the two measurement positions is always identical.

For the determination of the depth d of the impurity 5, calculated form the upper surface of the workpiece 1, initially a signal ratio is formed with the quotient of the two measurement signals of the first and the second measurement positions. with the aid of the graph according to FIG. 3, the determination of the depth is thus possible, whereby the graph gives the signal ratio along the abscissa and the depth along the ordinate. The associated arrows give, as is usual in graphs, the directions for values of increasing magnitude in the graph a curve 6, shown from which the relationship between the signal ratio and the depth of the impurity 5 in the workpiece 1 is given. It can be seen that the signal ratio is reduced as the depth increases. Based upon the detected signal ratio, the curve 6 gives the depth d.

The determination of the mass of the impurity can be effected, alternatively by the graph according to FIG. 4, or the graph according to FIG. 5. Initially the method with the graph according to FIG. 4 is explained.

In this graph, the abscissa indicates the measurement signal in a first measurement position and the ordinate the mass since there is no direct relationship between the measurement signal and the mass—the measurement signal being dependent not only from the mass of the impurity 5 but also from its depth d in the workpiece—a family of curves is shown in the graph and for example can be comprised of the three lines 7, 8, 9. The lines 7, 8, 9 are determined for impurities of different mass at the same depth. Line 7 with the steepest slope has a mean indicated by the triangles, for example at 11. symbolizing a measured value for impurities of a reduced depth. Correspondingly the intermediate line 8 has a mean represented by the squares 12 whereby impurities of different gasses in an intermediate plane are detected. The lower line 10 represents the depth d. Here the measured values are indicated by points, for example, at 13. The depths of the impurities for determining the line 10 are here still greater than for the line 9.

With the aid of graph of FIG. 4, a mass e of the impurity 5 can be detected by marking off the respective point along the line 10 which lie at the level of the measurement signal in the first measurement position. As a result the value e is obtained for the mass.

In the graph of FIG. 5, the measurement signal is displayed as a function of depth. For this purpose as well a family of curves exists which represents the mass with increasing values in the direction of the arrow. In the graph, for example, four curves 14, 15, 16, 17 are shown. The measurement signal is logarithmically applied.

Each curve represents the relationship between measurement signal and depth at a constant mass since the depth is known with the aid of the graph according to FIG. 3 as much as is the measurement signal in the first measurement position, the respective curve 14, 15, 16, 17 can be obtained by marking off the abscissa and the ordinate.

In the present example, the curve 15 is the curve representing the mass e. It will be understood that the afore-described type of determination of the depth d of the impurity 5 and its mass e serves only to enable understanding of the invention. In the construction of the magnetic-field measuring device, the above-described relationship can be stored, for example, in a microprocessor after carrying out a calibration, whereby the calculation of the depth and the mass is effected with the aid of a computer program on the basis of the stored relationship. Thus the curves 6, 7, 8, 9, 14, 15, 16, 17 are stored as functions in the form of a matrix or in another way known in the art. It will be understood further that the computer program can enable interpolation for values for which there are no lines in the family of curves of FIG. 4 for the determination of the depth d and no curves in the family of curves of FIG. 5 for the mass 5.

In FIG. 6, the magnetic field sensor 3 is scannable over the workpiece 1 and movable relative to a surface of the workpiece, as has been described, for juxtaposition with the workpiece at a first distance from the surface of the workpiece to obtain a first signal measuring magnetic field strength derived from the ferromagnetic impurity after the impurity has been magnetized in the magnetic field and at a second distance from the surface different from the first (compare FIGS. 1 and 2) to obtain a second signal measuring magnetic field strength derived from the ferromagnetic impurity. The magnetic field strength measurement are effected at 20. A ratio former 21 constitutes means for forming a signal ratio of the first and second signals as a quotient of the magnetic field strength at the first and second distances. Means 22 determines from a curve in which the dependency of the signal ratio is plotted against impurity depth based upon the signal ratio, the depth of the impurity in the workpiece (see FIG. 3).

A storage 23 for the family of curves of different depths is connected to the depths determination means 22 which also constitutes the means for calculating the mass of the impurity from the family of curves by selection of the curve corresponding to the determined depth and based upon the measurement.

The storage means 23 can store a family of curves of different masses of impurity to give the dependency between depth and measurement signal for different masses.

What is claimed is:

1. A method of determining a depth of a ferromagnetic impurity in a workpiece of a nonmagnetic material, comprising the steps of:
   (a) magnetizing said ferromagnetic impurity uniformly by subjecting said workpiece at least in sections to a magnetic field;
   (b) thereafter juxtaposing said workpiece and a magnetic field measuring sensor at a first distance from a surface of said workpiece to obtain a first signal measuring magnetic field strength deriving from said ferromagnetic impurity;
   (c) then juxtaposing said workpiece and said magnetic field measuring sensor at a second distance from said surface of said workpiece different from said first distance to obtain a second signal measuring magnetic field strength deriving from said ferromagnetic impurity;
   (d) forming a signal ratio of said first and second signals as a quotient of the magnetic field strengths at said first and second distances; and
   (e) based upon said signal ratio, determining from a curve in which the dependency of the signal ratio is plotted against an impurity depth, a depth of the impurity in said workpiece from which the magnetic field strengths were measured.

2. The method defined in claim 1 wherein said impurity is magnetized in step (a) to saturation.

3. The method defined in claim 2, further comprising the step of demagnetizing said workpiece prior to magnetization of said ferromagnetic impurity in step (a).

4. The method defined in claim 3 wherein said magnetic field is a substantially homogeneous magnetic field.

5. The method defined in claim 3, further comprising the step of relatively moving said workpiece and said sensor to scan said sensor over said workpiece.

6. The method defined in claim 3, further comprising determining a mass of said impurity by selecting a curve for determining depth from a family of curves which display a relationship between mass and measurement signal for different depths and selecting the mass based upon the measurement signal and the selected curve.

7. The method defined in claim 3, further comprising the step of determining the mass of the impurity by selecting a particular curve from a family of curves giving a relationship between depth and measurement signal at different masses.

8. An apparatus for determining a depth of a ferromagnetic impurity in a workpiece of a nonmagnetic material comprising:
   means for magnetizing said ferromagnetic impurity uniformly by subjecting said workpiece at least in sections to a magnetic field;
   a magnetic field sensor scannable over said workpiece and movable relative to a surface of said workpiece for juxtaposition with said workpiece at a first distance from said surface of said workpiece to obtain a first signal measuring magnetic field strength derived from said ferromagnetic impurity after said ferromagnetic impurity has been magnetized in said magnetic field, and at a second distance from said surface different from said first distance to obtain a second signal measuring magnetic field strength derived from said ferromagnetic impurity;
   means for forming a signal ratio of said first and second signals as a quotient of said magnetic field strength at said first and second distances; and
   means for determining from a curve in which the dependency of the signal ratio is plotted against impurity depth, based on said signal ratio of said first and second signals a depth of the impurity in the workpiece from which the magnetic field strengths were measured.

9. The apparatus defined in claim 8, further comprising a storage for a family of curves of different depths giving the dependency between mass of the impurity and a measurement signal at different depths, and means for calculating the mass of the impurity from the family of curves by selection of the curve corresponding to the determined depth and based upon the measurement signal.

10. The apparatus defined in claim 9, further comprising means for storing a family of curves of different masses of impurity and giving a dependency between depth and measurement signal for different masses, and means for calculating the mass of the impurity by selecting one of said curves based upon the determined depth and on the measured signal.

* * * * *